United States Patent [19]

Siegers

[11] Patent Number: 4,624,668
[45] Date of Patent: Nov. 25, 1986

[54] METHOD FOR COTTONWOOL TAMPON

[75] Inventor: Hans P. Siegers, Wegberg, Fed. Rep. of Germany

[73] Assignee: Henkel Kommanditgesellschaft auf Aktien, Duesseldorf, Fed. Rep. of Germany

[21] Appl. No.: 573,082

[22] Filed: Jan. 23, 1984

[30] Foreign Application Priority Data

Jan. 24, 1983 [DE] Fed. Rep. of Germany ....... 3302193

[51] Int. Cl.$^4$ .............................................. A61F 13/16
[52] U.S. Cl. .................................... 604/904; 604/358
[58] Field of Search ................ 604/904, 377, 378, 358

[56] References Cited

U.S. PATENT DOCUMENTS 3,322,123 5/1967 Griswold et al. .................... 604/904
4,266,546 5/1981 Roland et al. ........................ 604/904
4,359,357 11/1982 Friese ................................... 604/904

Primary Examiner—Stephen C. Pellegrino
Assistant Examiner—Sherri E. Vinyard
Attorney, Agent, or Firm—Ernest G. Szoke; Henry E. Millson, Jr.; Mark A. Greenfield

[57] ABSTRACT

A method of making a cottonwool tampon incorporating a recovery cord in which a length of cottonwool strip is wrapped in a fluff-free covering material without any accumulations of material or seams being necessary or being formed at the front end. According to the invention, a curtain of covering material is draped into the feed path of the length of cottonwool strip in such a way that, as the cottonwool strip advances, the covering material is folded around its leading edge and is applied to the upper and lower surfaces of the length of the cottonwool strip.

14 Claims, 2 Drawing Figures

METHOD FOR COTTONWOOL TAMPON

This invention relates to a method of making a cottonwool tampon incorporating a recovery cord, in which a length of cotton wool is wrapped in a fluff-free covering material, more particularly in the form of a nonwoven fabric.

BACKGROUND OF THE INVENTION

In tampons of this type hitherto used in feminine hygiene, fibres or pieces of cottonwool can remain behind in the vagina. Accordingly, attempts have been made in the manufacture of tampons to wrap the fibrous cottonwool plug in a fluff-proof covering. A covering such as this may consist, for example, of rayon, synthetic fibers or of a mixture of these materials, preferably in the form of a nonwoven fabric. For example, tampons are made by a process in which the rectangular length of cottonwool strip is wrapped in a nonwoven fabric and the associated recovery cord or thread is stitched on longitudinally to the strip. To prevent the release of fluff, the elements thus prepared are compressed in various directions and/or sealed or welded or adhesively bonded, particularly at the edges.

DESCRIPTION OF THE INVENTION

The object of the present invention is to wrap a length of cottonwool strip in a covering material (to prevent the release of any fluff) in such a way that, at the front end of the tampon opposite the rear end where the recovery cord is attached, there are neither any accumulations of material, as in compression, nor any seams, as in circular sealing.

This object is achieved in accordance with the invention by draping the covering material vertically like a curtain into the transport path of the cottonwool strip centrally in front of its leading edge, so that, by advancing the cottonwool strip, the curtain of covering material is folded around the leading edge and also applied to the upper and lower surfaces of the cottonwool strip, and wherein the edges of the covering material abutting one another along the side edges of the cottonwool strip laterally adjoining the leading edge are joined seamlessly to one another in fluff-proof manner.

At its front end, a tampon made in accordance with the invention is shaped very favorably to absorb liquid because there are no accumulations of materials nor any seams there. Another advantage of the method according to the invention lies in the fact that the apparatus required for introducing the curtain of covering material, particularly the unrolling units and cutters, fits compactly into the tampon machine.

The length of cottonwool strip to be wrapped in covering material in accordance with the invention has two or four cut edges, as in the preparatory stages of the manufacture of compressed tampons. A sealable nonwoven fabric, e.g. rayon, synthetic fibers, or a mixture of such materials, weighing from 10 to 20 g/m² is advantageously used as the covering.

The length of cottonwool strip can be introduced into the covering material immediately before the recovery cord is stitched on. However, it is more desireable to fasten the recovery cord, more particularly by sewing, to the length of cottonwool strip before it is introduced into the covering material. The reason for this is that, in this case, the recovery cord is situated inside the covering and, accordingly, does not appear on the outer surface or, more particularly, on the front edge of the finished tampon.

The embodiment of the invention is described in detail in the following with reference to the drawings.

Figure 1:
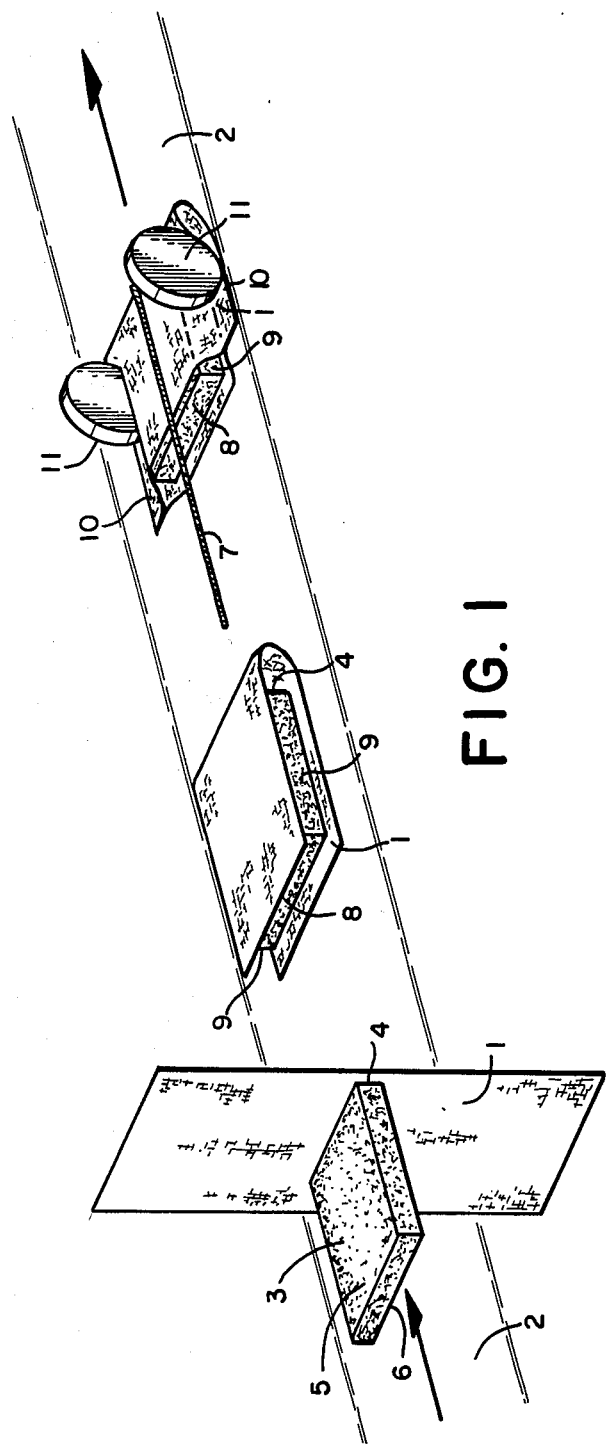
FIG. 1 is a schematic drawing of the steps of the present method for making a cottonwool tampon having an external recovery cord.

FIG. 1 shows steps involved in the manufacture of a tampon formed with an external recovery cord.

Figure 2:
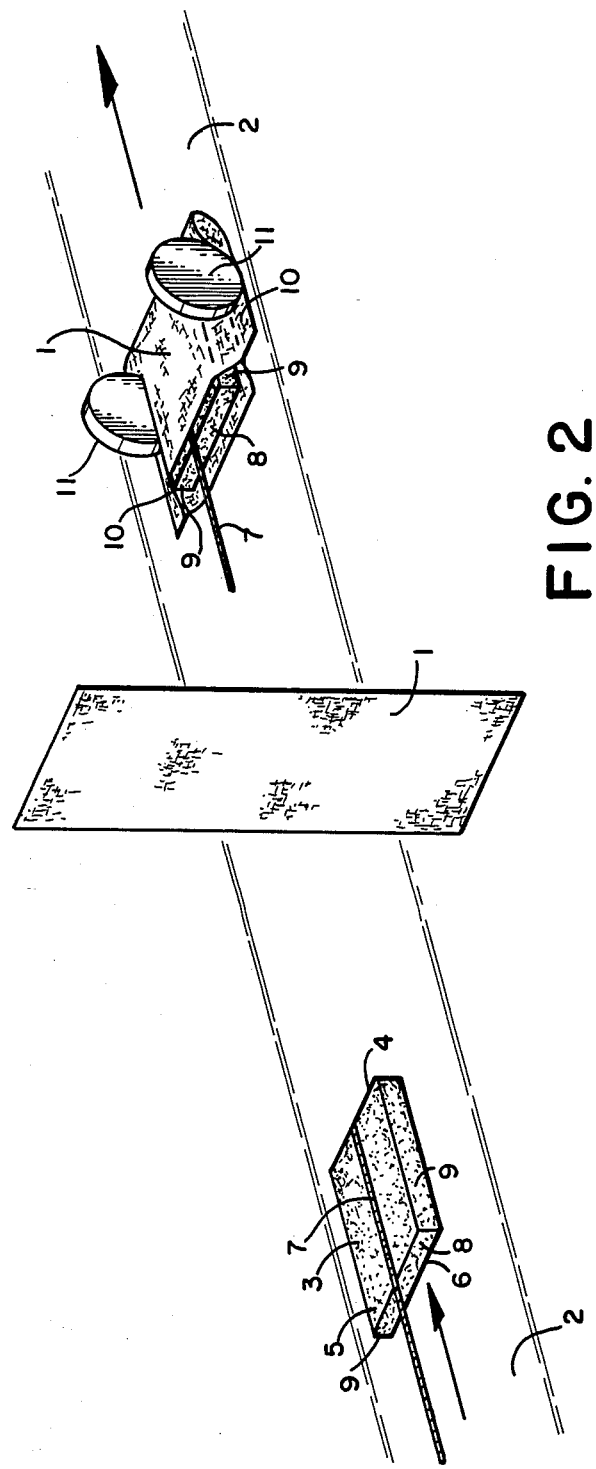
FIG. 2 is a schematic drawing of the steps of the present method for making a cottonwool tampon having an internal recovery cord.

FIG. 2 shows steps involved in the manufacture of a tampon formed with an internal recovery cord.

In the manufacturing steps illustrated in FIGS. 1 and 2, covering material 1 is draped vertically like a curtain across the arrowed transport path 2 of a section 3 of a cottonwool strip which has already been cut from a longer strip of cottonwool. Cottonwool section 3 is then moved so that its front edge 4 centrally contacts the curtain of covering material 1 in such a way that the covering material covers the upper and lower surfaces 5 and 6 of the length of cottonwool section 3. In the variant shown in FIG. 1, cottonwool section 3 is introduced into the curtain of covering material 1 before the recovery cord 7 is sewn on. Accordingly, recovery cord 7 appears on the outer surface of the end product. In the variant illustrated in FIG. 2, recovery cord 7 is sewn on before cottonwool section 3, provided with the recovery cord 7, is introduced into the curtain of covering material 1. In this variant, recovery cord 7 is only visible at rear end 8 of the end product.

At the sides 9 of cottonwool section 3, portions 10 of covering material 1 project beyond the lateral edges of sides 9. Portions 10 of covering material 1 are sealed by means of sealing rollers 11. Instead of sealing rollers 11, sealing tongs, adhesive or other means (not shown) can also be used for forming the seamless joint. If it is deemed necessary or desireable to seal rear end 8 of cottonwool section 3, covering material 1 is formed with a length such that it projects beyond rear end 8 approximately 5 mm from both upper and lower surfaces 5 and 6 of cottonwool section 3. If it is not sufficient to press this projecting material against the end of the tampon, a seamless joint can be formed in this zone also by means of a sealing band, by means of adhesive bonding, in the same manner as at the sides, or the like.

The tampons produced by the processes of FIGS. 1 and 2 are then shaped by conventional means (not shown) into a normal cylindrically shaped unit prior to packaging and shipment.

What is claimed is:

1. A method for the manufacture of a fluff-free cottonwool tampon having a section of cottonwool encased in a fluff-free covering material and a recovery cord associated therewith comprising:
   (a) moving a section of cottonwool having at least a top, front edge, and bottom in a horizontal path;
   (b) draping a sheet of fluff-free covering material, whose surface area is sufficient to cover the combined surface areas of the top, forward edge, and bottom of said section, directly in the path of said moving section, in a plane perpendicular to the direction of movement of said section;
   (c) butting the forward edge of said section against the approximate center of said sheet;

(d) continuing the forward motion of said section until said sheet is wrapped around the top, forward edge, and bottom surfaces of said section and extends a substantially uniform distance beyond each lateral edge of said section other than said forward edge;

(e) joining together by seamless attachment the pair of top and bottom covering material extensions present on each side edge of said section; and (f) attaching a recovery cord to the tampon by associating said cord with said tampon before said section has been encased by said sheet.

2. The method of claim 1 wherein said recovery cord is attached by sewing.

3. The method of claim 1 wherein said seamless attachment is by sealing with sealing rollers.

4. The method of claim 1 wherein the covering material extensions present at each rear edge of said section are sealed by means of a sealing band or adhesive.

5. The method of claim 1 wherein the covering material extensions present at each rear edge of said section are pressed against the rear end of said section.

6. The method of claim 1 wherein the covering material extensions present at each rear edge of said section are sealed in the same manner as said side edges.

7. The method of claim 1 wherein said sheet comprises a non-woven synthetic fiber material weighing about 10–20 g/m$^2$.

8. A method for the manufacture of a fluff-free cottonwool tampon having a section of cottonwool encased in a fluff-free covering material and a recovery cord associated therewith comprising:

(a) moving a section of cottonwool having at least a top, front edge, and bottom in a horizontal path;

(b) draping a sheet of fluff-free covering material, whose surface area is sufficient to cover the combined surface areas of the top, forward edge, and bottom of said section, directly in the path of said moving section, in a plane perpendicular to the direction of movement of said section;

(c) butting the forward edge of said section against the approximate center of said sheet;

(d) continuing the forward motion of said section until said sheet is wrapped around the top, forward edge, and bottom surfaces of said section and extends a substantially uniform distance beyond each lateral edge of said section other than said forward edge;

(e) joining together by seamless attachment the pair of top and bottom covering material extensions present on each side edge of said section; and (f) attaching a recovery cord to the tampon by associating said cord with said tampon after said section has been encased by said sheet.

9. The method of claim 8 wherein said recovery cord is attached by sewing.

10. The method of claim 8 wherein said seamless attachment is by sealing with sealing rollers.

11. The method of claim 8 wherein the covering material extensions present at each rear edge of said section are sealed by means of a sealing band or adhesive.

12. The method of claim 8 wherein the covering material extensions present at each rear edge of said section are pressed against the rear end of said section.

13. The method of claim 8 wherein said wherein the covering material extensions present at each rear edge of said section are sealed in the same manner as said side edges.

14. The method of claim 8 wherein said sheet comprises a non-woven synthetic fiber material weighing about 10–20 g/m$^2$.

* * * * *